United States Patent [19]

Jones

[11] Patent Number: 4,795,426
[45] Date of Patent: Jan. 3, 1989

[54] CATHETER INTRODUCING DEVICE AND METHOD OF PLACING CATHETER

[75] Inventor: Jeffrey S. Jones, Salem, Va.

[73] Assignee: Solutech, Inc., Roanoke, Va.

[21] Appl. No.: 34,281

[22] Filed: Apr. 2, 1987

[51] Int. Cl.⁴ ............................................. A61M 31/00
[52] U.S. Cl. ...................... 604/51; 604/281; 604/175; 604/256; 137/223
[58] Field of Search ............... 604/281, 247, 167–169, 604/96, 256, 236, 53, 8–10, 280, 283–289, 164, 175, 51–53; 137/223

[56] References Cited

U.S. PATENT DOCUMENTS

| | | | |
|---|---|---|---|
| 3,902,517 | 9/1975 | Hastwell | 137/223 |
| 3,970,089 | 7/1976 | Stice | 604/256 |
| 4,000,739 | 1/1977 | Stevens . | |
| 4,023,559 | 5/1977 | Gaskell | 604/280 |
| 4,106,497 | 8/1978 | Percarpio . | |
| 4,160,450 | 7/1979 | Doherty . | |
| 4,235,232 | 11/1980 | Spaven et al. . | |
| 4,239,042 | 12/1980 | Asai . | |
| 4,387,879 | 6/1983 | Tauschinski . | |
| 4,447,237 | 5/1984 | Frisch et al. | 604/256 |
| 4,643,733 | 2/1987 | Becker | 623/11 |
| 4,645,504 | 2/1987 | Byers | 623/11 |
| 4,662,883 | 5/1987 | Bell et al. | 623/8 |

Primary Examiner—C. Fred Rosenbaum
Assistant Examiner—Colleen Reilly
Attorney, Agent, or Firm—Lathrop & Clark

[57] ABSTRACT

A catheter placement cannula is disclosed having a passageway therethrough to receive a catheter. The cannula is made up of a substantially tubular body portion and a tip portion made of pliable material. The tip portion has a shape retaining memory such that the end of the tip is naturally flattened in shape to provide a seal for preventing the backflow of blood or other fluids when the cannula is in place in a body.

7 Claims, 1 Drawing Sheet

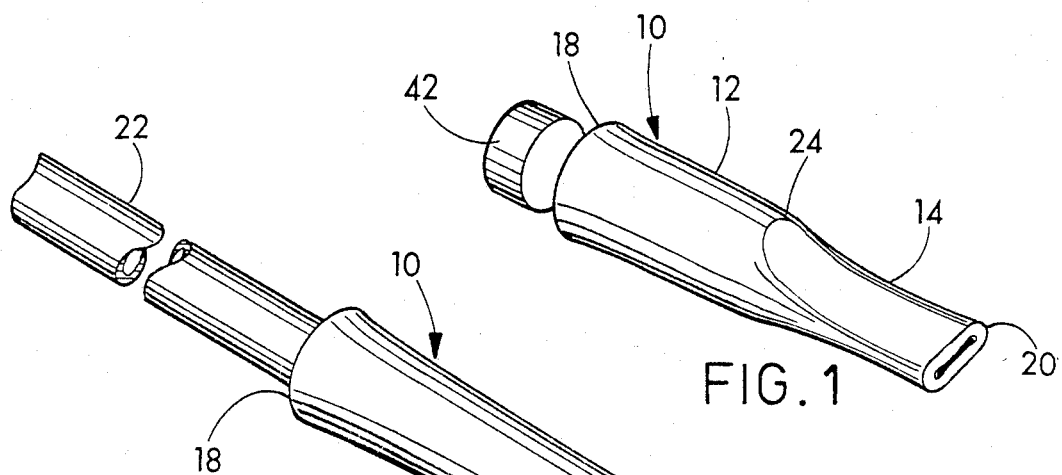
FIG. 1
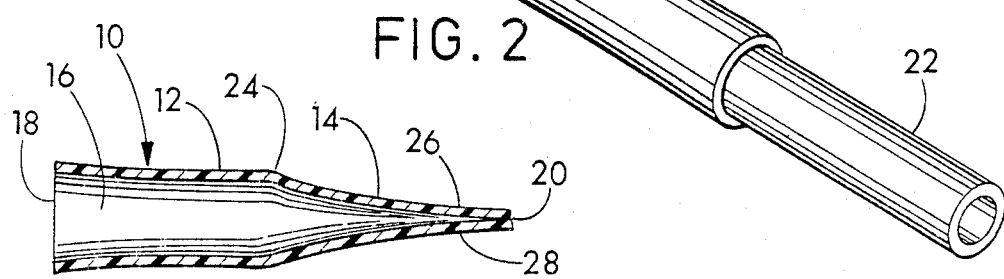
FIG. 2
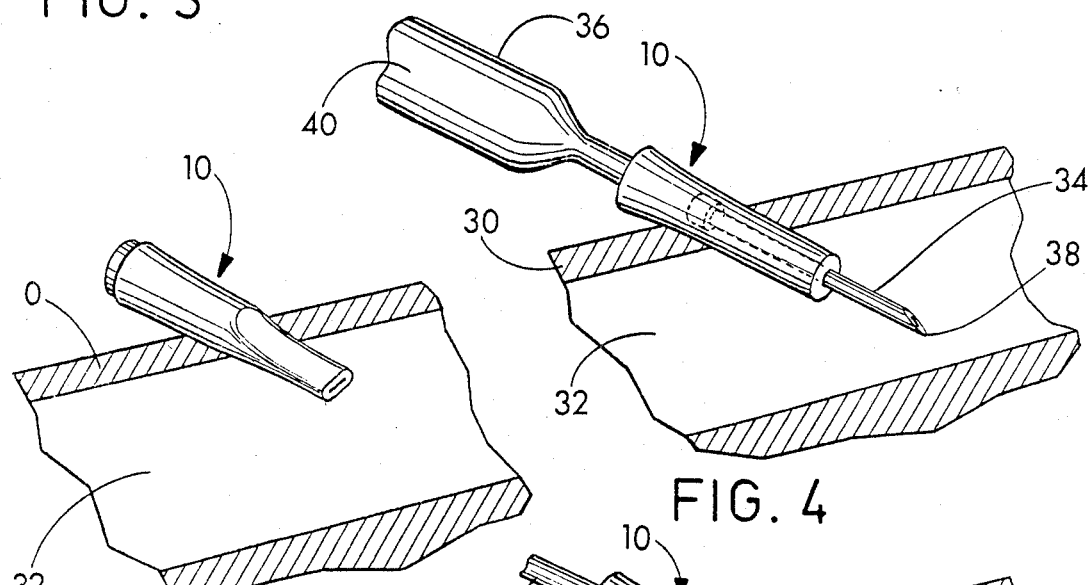
FIG. 3
FIG. 4
FIG. 5
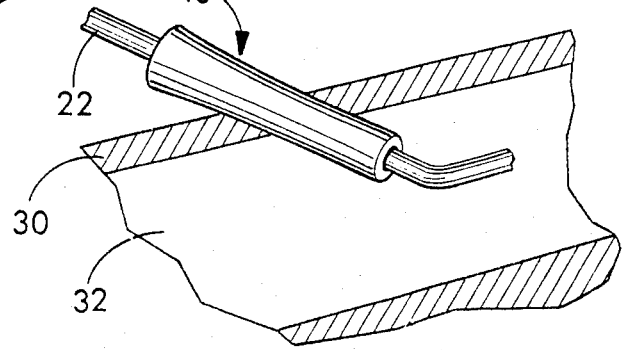
FIG. 6

CATHETER INTRODUCING DEVICE AND METHOD OF PLACING CATHETER

BACKGROUND OF THE INVENTION

1. Field of the Invention

The present invention relates to catheters in general and particularly to cannulas for introducing catheters into a body.

2. Description of the Prior Art

Catheters have a variety of uses especially in the medical field. The term "catheter" is commonly used to identify a tubular instrument that is inserted into various body cavities, either naturally or surgically opened. They can be used for administering fluids into the body, performing blood transfusions, removal of body fluids or components of body fluids, blood pressure determinations, etc.

Conventionally, a catheter is placed into the, body-by any of a number of well known methods. The simplest method is to make a surgical incision in the body and insert the tip of the catheter directly through the incision into the body. Alternatively, a needle is inserted into the body and the catheter is passed through the needle and into the body. The needle is then usually withdrawn leaving the catheter inserted. These methods inevitably involve the loss of blood through the incision. Further, the damage to the skin, blood vessel wall and other body parts makes it difficult to employ the same area when multiple studies are contemplated.

Semi-permanent cannulas are also known. The term "cannula", as it is used here, means a generally tubular device, through which a catheter is placed, which is designed to assist the placement of the catheter in the body. For example, U.S. Pat. No. 4,000,739 to Stevens is directed to a cannula which is adapted to be left in place in the body whether or not a catheter is present. A gasket-like seal having a Y-shaped slit is placed in the cannula in order to prevent any backflow of blood when a catheter is removed. U.S. Pat. No. 4,239,042 to Asai is directed to a catheter placement system which involves a cannula having a body portion and a tip portion. The cannula is useful in avoiding thrombogenic irritations and in avoiding collapse of the catheter during use. However, these patents suffer the disadvantage of being of a relatively large size. Additionally, they are quite bulky to use, often requiring more than one pair of hands for insertion and use.

SUMMARY OF THE INVENTION

It is the purpose of the present invention to provide a catheter placement device or cannula which avoids the above-noted problems. The device of the present invention is contemplated by a cannula for placing a catheter in a body comprising a body portion made of material of sufficient rigidity to receive the catheter and a tip portion made of a pliable material of sufficient rigidity to also receive the catheter. The tip portion is connected to the body portion and has a shape retaining memory such that the tip is naturally flattened in a sealed condition when not in use. This has the direct advantage of preventing any backflow of blood or other fluids from the body when a catheter is removed leaving only the cannula in place. Additionally, once the cannula of the present invention is inserted into the body, it can remain in the body for multiple uses or studies. By this, it is meant that the cannula of the present invention may be used for successive catheter insertions. This has the advantage of requiring only one puncture into the body for multiple studies. Due to the relatively small size of the cannula it may be placed in virtually any part of the body. The term "body" as used herein is specifically directed to a human body but it is to be understood that the device of the present invention is useful in other types of bodies, such as animals other than humans.

Further, the use of the cannula of the present invention aids in avoiding the collapse of the catheter during placement and use.

The cannula of the present invention can advantageously be left in the body whether a catheter is or is not present. When the catheter is in place, there is no blood loss due to the sealing engagement between the interested catheter and the cannula walls. When the catheter is removed, the tip of the cannula automatically closes obviating the necessity of either removing the cannula or of occluding the cannula.

DESCRIPTION OF THE DRAWINGS

FIG. 1 is a side perspective view of the cannula of the present invention in closed position.

FIG. 2 is a side perspective view of the cannula of the present invention with a catheter-like device in place.

FIG. 3 is a cross-sectional side view of the cannula of FIG. 1.

FIG. 4 is a schematic view of a method of placing the cannula into a body.

FIG. 5 is a side perspective view of the cannula of the present invention in place in a body.

FIG. 6 is a side perspective view of the cannula of the present invention in place in the body with a catheter.

DETAILED DESCRIPTION OF THE INVENTION

FIGS. 1 and 2 show the cannula 10 according to the present invention. Cannula 10 is made of a material having sufficient rigidity to be inserted into a body part such as, for example, a blood vessel, through an opening made by a needle tip. Cannula 10 must have enough rigidity to withstand the pressure from the patient's skin and the systemic pressure against it after the cannula insertion device is withdrawn. All or part of cannula 10 may be composed of any standard flexible, nontoxic materials, such as for example natural rubber or latex, polypropylene, fluororesin, polyethylene, polyvinylchloride or silicone. The surface of cannula 10 may also be coated with a low-friction material in order to eliminate the tendency to grab the skin tissues and to prevent a build up of infection-causing organisms. Materials such as Teflon ® and silicone act to create a low-friction surface.

If desired, part of cannula 10 may be made of metals such as stainless steel as will be described further on in this description. Cannula 10 comprises a body portion 12 and a tip portion 14. Body portion 12 and tip portion 14 are a generally one piece construction of extruded flexible material as described above. However, it is contemplated in this invention to have separate body portions 12 and tip portions 14. In this manner, body portion 12 may be made of a material which is different from tip portion 14. For example, body portion 12 may be made of hard plastics or metals in a generally tubular fashion. Tip portion 14, on the other hand, must be made of a generally pliable material. As illustrated in the figures, the proximal portion 18 of the body 12 is flared to accommodate the catheter 22. In this manner, a catheter having a diameter only slightly smaller than the cannula, as illustrated in FIG. 2, may be easily inserted into the cannula.

Cannula 10 has a passage 16 therethrough adapted to receive a catheter. As illustrated in FIG. 3, passage 16 extends from the proximal portion 18 of the cannula 10 to the distal end 20 of the tip 14. However, due to the memory-activated closure of the tip 14, passage 16 is normally sealed off when a catheter 22 or other object is not in place in the cannula 10.

The tip 14 acts as a backflow prevention valve. Like body portion 12, it contains passage 16. However, the tip 14 is provided with a "memory" of a naturally closed seal as illustrated in FIGS. 1, 3 and 5. This seal is capable of withstanding minimum blood pressure or other fluid pressure when a catheter is removed. The normally closed tip is adapted when closed to prevent any fluid from flowing through passage 16 of the cannula 10. This obviates the necessity of occluding the cannula and also prevents significant blood or fluid loss at all times.

When desired, the valve may be shifted from the normally closed position to an open position, as illustrated in FIGS. 2 and 6. The tip is generally formed of a cylindrical hollow base portion at 24 with a pair of tapered opposing flaps 26 and 28 which are engaged in a sealing relationship at the distal end 20 when the tip portion is in a normal relaxed position.

When a catheter 22 or other object is inserted into the cannula 10, as illustrated in FIG. 2, the resilient walls of the tip 14 adjust to allow the passage of the catheter 22. The walls of the tip 14 are so provided to be in sealing engagement with the catheter 22 in order to prevent any back flow of body fluid through the passage 16 when the catheter 22 is in place.

One method of inserting the cannula of the present invention into a body will be described below, with specific reference to FIG. 4. FIG. 4 shows a cross-sectional view of the skin 30 and a blood vessel 32 of a patient. In operation, an incision is made in the patients skin 30 close to the blood vessel 32 to be used. Cannula 10, which is fitted with a needle 34 of the cannula insertion device 36 is then introduced into the blood vessel 32. When the tip 38 of the needle 34 reaches the blood vessel, blood spurts through the hollow portion of the needle and appears in the syringe 40, which confirms that the cannula and needle have penetrated into the vein. The cannula insertion device 36 consisting of the syringe 40 and the needle 34 is then withdrawn, leaving the cannula 10 in the body as illustrated in FIG. 5.

It is to be understood that the body portion 12 of the cannula 10 may be of any length as desired. Generally, the body portion 12 is affixed to the skin surface by any means known to the art, such as an adhesive strip. When the cannula is not in use, a plug 42 may be placed on the proximal end of the cannula 10 in order to prevent the 15 entrance of any bacteria or other infectious organisms into the passageway 16.

When it is desired to place the catheter 22 through the cannula 10 into the blood vessel 32, the plug 42 is simply removed and the catheter 22 is passed through the passageway 16 of the cannula 10. The resiliency of the tip 14 will immediately cause the tip 14 to adjust to the entrance of the catheter 22 allowing its passage therethrough and into the blood vessel 32 as illustrated in FIG. 6.

If multiple studies are indicated, it is a simple matter to remove the catheter 22 and introduce another. The sealing nature of the naturally closing tip 14 will prevent any clotting. However, in order to further insure the prevention of clotting, an anticoagulant such as heparin may be flushed through the passage 16.

By the cannula 10 of the present invention, multiple insertions of catheters may be made in one incision in the body. This removes the necessity of multiple incisions.

Although the present invention has been described with preferred embodiments, it is to be understood that modifications and variations may be resorted to, without departing from the spirit and scope of this invention, as those skilled in the art will readily understand.

I claim:

1. A cannula for placing a catheter or the like in an animal comprising:
   (a) a substantially tubular body portion having sufficient rigidity for placement in the animal, the body portion having a passageway therethrough, the body portion being made of a material of sufficient rigidity to receive the catheter and, the body portion further having a flared proximal end for easily receiving the catheter; and
   (b) a self-sealing substantially straight tip portion made of pliable material of sufficient rigidity to receive the catheter, the tip portion being connected to the body portion, the tip portion being formed of opposing flaps, wherein the tip portion has a shape retaining memory to form a seal.

2. The cannula according to claim 1 wherein the body portion is pliable.

3. The cannula according to claim 1 wherein the body portion and the tip portion are formed of the same material.

4. The cannula according to claim 1 wherein the composition of the cannula is selected from the class of material consisting of polyethylene, rubber, latex, polypropylene, fluororesin, silicone and polyvinylchloride.

5. The cannula according to claim 1 in combination with the catheter, wherein the catheter is in sealing engagement with the cannula.

6. A method of introducing a catheter or the like into an animal comprising:
   (a) inserting a cannula into an opening in the animal, said cannula comprising a substantially tubular body portion having sufficient rigidity for placement in the animal, the body portion having a passageway therethrough, the body portion being further made of a material of sufficient rigidity to receive the catheter, wherein the body portion has a flared proximal end for easily receiving the catheter; and a resilient self-sealing substantially straight tip portion connected to the body portion, the tip portion having sufficient rigidity to receive the catheter, wherein the tip portions has a shape retaining memory such that the tip portion is naturally flattened to form a seal; and
   (b) passing the catheter through the body portion and tip portion of the cannula, such that the resiliency of the tip portion adjusts the shape retaining memory to allow the catheter to pass therethrough into the animal.

7. The method according to claim 6 wherein the catheter is in sealing engagement with the cannula.

* * * * *